United States Patent [19]

Jacobson et al.

[11] Patent Number: 5,503,840
[45] Date of Patent: Apr. 2, 1996

[54] ANTIMICROBIAL COMPOSITIONS, PROCESS FOR PREPARING THE SAME AND USE

[75] Inventors: Howard W. Jacobson; Michael H. Scholla; Annie W. Wigfall, all of Wilmington, Del.

[73] Assignee: E. I. Du Pont de Nemours and Company, Wilmington, Del.

[21] Appl. No.: 139,962

[22] Filed: Oct. 20, 1993

Related U.S. Application Data

[63] Continuation-in-part of Ser. No. 6,022, Jan. 15, 1993, abandoned, which is a continuation of Ser. No. 742,963, Aug. 9, 1991, Pat. No. 5,180,585.

[51] Int. Cl.$^6$ ................................................ A01N 25/26
[52] U.S. Cl. ..................... 424/421; 424/405; 424/404; 424/618; 424/630; 424/641
[58] Field of Search ............................... 424/405, 404, 424/421, 490, 619, 635, 724

[56] References Cited

U.S. PATENT DOCUMENTS

| | | | |
|---|---|---|---|
| 3,625,771 | 12/1971 | Arrance et al. | 136/145 |
| 3,785,798 | 1/1974 | Horai et al. | 71/79 |
| 4,464,317 | 8/1984 | Thies et al. | 264/4.3 |
| 4,525,410 | 6/1985 | Hagiwara et al. | 428/178 |
| 4,741,779 | 5/1988 | Mita et al. | 106/288 |
| 4,775,585 | 10/1988 | Hagiwara et al. | 428/323 |
| 5,122,418 | 6/1992 | Nakane et al. | 424/401 |
| 5,180,585 | 1/1993 | Jacobson et al. | 424/405 |

FOREIGN PATENT DOCUMENTS

| | | |
|---|---|---|
| 0253663 | 7/1986 | European Pat. Off. . |
| 0251783 | 1/1988 | European Pat. Off. . |
| 0488269 | 6/1992 | European Pat. Off. . |
| 62-070221 | 3/1987 | Japan . |
| 80106758 | 8/1991 | Taiwan . |
| 059193 | 2/1993 | Taiwan . |

*Primary Examiner*—Thurman K. Page
*Assistant Examiner*—Neil Levy
*Attorney, Agent, or Firm*—Michael K. Boyer

[57] ABSTRACT

An antimicrobial composition of titanium dioxide, barium sulfate, zinc oxide particles, and mixtures thereof having successive coatings of silver, in some cases a coating of zinc and/or copper compounds such as zinc oxide, copper (II) oxide and zinc silicate; silicon dioxide; alumina; and a dispersion aid such as dioctyl azelate.

13 Claims, No Drawings

ANTIMICROBIAL COMPOSITIONS, PROCESS FOR PREPARING THE SAME AND USE

CROSS REFERENCE TO EARLIER FILED PATENT AND APPLICATION

This application is a Continuation-In-Part of U.S. patent application Ser. No. 08/006,022, filed Jan. 15, 1993, now abandoned which in turn is a continuation of U.S. patent application Ser. No. 07/742,963, filed Aug. 9, 1991, now U.S. Pat. No. 5,180,585; the disclosure of the previously identified documents is hereby incorporated by reference

FIELD OF THE INVENTION

The present invention relates to an improved antimicrobial powder composition of a mixture of titanium dioxide and barium sulfate particles having successive coatings of silver, silicon dioxide, alumina, dioctyl azelate, among other coatings

BACKGROUND OF THE INVENTION

Polymeric articles having antimicrobial properties are described in the literature. Such articles are made in various shapes and dimensions such as granules, films, fibers, containers, pipes, structural components, medical appliances, among other articles. It is also known that certain metals such as silver, copper and zinc or their compounds are effective as antimicrobial agents. Numerous attempts have been made to utilize this attribute in polymeric articles.

For example, U.S. Pat. No. 4,906,466 describes an antimicrobial composition comprising a silver compound, selected from AgCl, AgBr, $Ag_2Co_3$ and $Ag_3PO_4$, deposited on a physiologically inert particle, selected from oxides of Ti, Mg, Al, Si, Ce, Hf, Nb and Ta, calcium hydroxyapatite and barium sulfate. It is disclosed that the compositions may be modified by the inclusion of other ingredients such as dispersion aids, and these compositions may be incorporated in polymeric materials in an amount of from 5-60% by weight of the composite. The antimicrobial silver compound in contact with the polymer article may interact with it producing undesirable effects, such as darkening due to reduction to metallic silver.

Several patents describe antimicrobial compositions in which zeolite particles are supports for antimicrobial metal ions. Zeolites are aluminosilicates, of either natural or synthetic origin, which have sites at which cationic exchange may occur. By treating them with solutions of metal ions a desired antimicrobial metal ion can be substituted in the zeolite structure. Polymer articles having antimicrobial properties are made by incorporating the treated zeolites with the polymer or the zeolite can be mixed with the polymer and then treated with a solution of the desired antimicrobial metal ion. There are no barrier coatings on the particles to prevent interactions of the metal ions with the polymer, to control the rate of release of the antimicrobial species or to facilitate dispersion of the particles in the polymer article. For example, the use of the zeolite particles in polymer articles is described in detail in U.S. Pat. No. 4,775,585, and, more specifically, U.S. Pat. No. 4,525,410 is directed to fiber applications. Further it is recognized that zeolite powders tend to agglomerate and are inferior to dispersibility when mixed with resins. U.S. Pat. No. 4,741,779 adds fine silica, dry or as a sol, to provide a zeolite powder which has high free-flowability and low agglomerating properties. Such problems as aggregation and color development in polymer antimicrobial zeolite compositions are also addressed in J 01164722 which relates to the use of additives such as fatty acid salts to aid dispersion and UV-light absorbers to prevent color development.

It is most desirable that the antimicrobial additive be easily dispersible within the polymer matrix without any significant adverse effects on polymer properties. It is also desirable that the antimicrobial be effective in controlling microorganisms at economic levels of use and remain active for months or years. Most commercially available compositions suffer from several deficiencies in the end use. They are often agglomerated and therefore difficult to disperse in end use systems. In addition, in the end use systems, the antimicrobial component is in direct contact with the product matrix with which it may react, leading to deterioration in properties, development of coloring or staining and other undesirable features. The development of color occurs during the shaping process, i.e., producing a shaped polymeric article. The cause for color deterioration may be attributed to the high metal loadings of the prior art. There is a need for antimicrobial compositions which do not have these deficiencies particularly when they are incorporated in a polymer matrix. The composition of the present invention meets this need.

The disclosure of each of the above identified references is hereby incorporated by reference.

SUMMARY OF THE INVENTION

U.S. Pat. No. 5,180,585 describes the desirability of an antimicrobial additive to be easily dispersible within a polymer matrix without any significant adverse effects on polymer properties. Most commercially available compositions suffer from several deficiencies in the end use. Further improvements over the prior art compositions are desirable. There is a need for an antimicrobial composition which exhibits the desired color, delivers antimicrobial functionality and luster, and is easily dispersible within the polymer matrix. For white yarns, especially those used in residential carpets, color and the level of delustering are key to the end use properties of the yarns. An antimicrobial composition which introduces minimal color, e.g., exhibits whiteness, when producing a shaped polymeric article while minimizing delustering and maintaining a high level of antimicrobial activity is particularly desirable. The composition of the present invention meets this need.

The present invention relates to an antimicrobial composition of at least one of titanium dioxide, zinc oxide and barium sulfate particles having successive coatings of silver; in some cases at least one of copper compounds such as copper (II) oxide and zinc compounds such as zinc oxide and zinc silicate; silicon dioxide; alumina; and dioctyl azelate. When the particle is zinc oxide, in some cases the coating of at least one of copper and zinc compounds may be omitted. The properties of polymeric articles having antimicrobial properties are enhanced when the present improved antimicrobial composition is incorporated therein. Especially advantageous antimicrobial compositions exhibit improved whiteness, minimal effect on luster and maintain a high level of antimicrobial activity when incorporated into a polymer matrix. Upon further study of the specification and appended claims, further advantages of this invention will become apparent to those skilled in the art.

The antimicrobial powder composition of the invention is effective against a wide range of microorganisms such as bacteria, fungi, algae, protoza, viruses, among others.

DETAILED DESCRIPTION

The present invention relates to a novel particulate antimicrobial powder composition consisting essentially of at least one of titanium dioxide, zinc oxide, and barium sulfate particles having successive coatings from at least one member of silver; in some cases at least one of copper compounds, e.g., copper (II) oxide, and zinc compounds such as zinc, zinc oxide, and zinc silicate, e.g., $ZnSiO_3$; silicon dioxide; alumina, e.g., hydrous alumina; dioctyl azelate, among others. Generally, the presence of silver is effective to kill certain bacteria whereas zinc and copper compounds are effective to control growth of microbes such as mildew.

The inorganic particles, i.e., core material, consist essentially of at least one member from the group of titanium dioxide, zinc oxide, and barium sulfate particles. The average diameter of titanium dioxide normally ranges between about 0.005 and 1.5 microns, zinc oxide usually ranges from between about 0.1 and 3.0 microns, and barium sulfate ranges between about 0.05 to 3 microns. In general, titanium dioxide, zinc oxide and barium sulfate particles in the sub-micron size range are desirable because the resulting antimicrobial composition can be distributed more uniformly throughout, for example, a polymer matrix. Either or both crystalline forms, i.e., anatase or rutile, of titanium dioxide are suitable for use in the present invention. The index of refraction for futile titanium dioxide is about 2.71, and for anatase titanium dioxide ($TiO_2(A)$) the index is about 2.52. The index of refraction for barium sulfate is about 1.64 and the index for zinc oxide is about 2.0. By mixing appropriate proportions of anatase, ruffle, zinc oxide and barium sulfate particles, the luster of a polymeric article can be controlled to range from dull to bright. The ratio of these particles can range from about 0 to about 100 by weight, and is tailored in order to impart the desired luster, whiteness (delta E or distance from white) and antimicrobial properties to the surrounding matrix. For example, in the case of a fiber matrix the presence of a relatively large amount of titania particles tends to deluster the fiber whereas zinc oxide particles tend to reduce the delta E (increase whiteness).

Successive coatings are typically applied separately to the titanium dioxide, zinc oxide and barium sulfate particles by using any suitable precipitation process. In some cases, the coatings can be applied simultaneously to a mixture of core particles. The coated core particles can then be blended to form a mixture of coated core particles. While any suitable method can be used for blending the coated particles, a commercially available "v" blender is normally used.

The first coating upon the particles is a silver or silver compound that functions as the antimicrobial component. When appropriate, the second coating upon the particles is selected from at least one member of copper and zinc compounds such as zinc, zinc oxide, zinc silicate, e.g., $ZnSiO_3$, copper, copper oxide, e.g., $CuO$, mixtures thereof, among others. When the particle is zinc oxide, in some cases the second coating may be omitted. The presence of silver, for example, along with copper (II) oxide confers antimicrobial properties to the particles. In order to maximize antimicrobial properties, the antimicrobial component should release silver, zinc and/or copper ions at an effective level of antimicrobial activity, e.g., a minimum of 2 log reduction within 24 hours in a shake flask test, over a prolonged period, such as months or usually years. The amount of antimicrobial component on the core particle ranges from about 0.1% to at least about 5% by weight; normally about 0.2% to about 1% by weight based on the particle core material.

A surprising and unexpected feature of the present invention is that the antimicrobial powders confer activity at loadings of the antimicrobial component which is substantially lower than those predicted by conventional materials. This feature is achieved despite the use of a protective coating, e.g., silica, to encapsulate the antimicrobial component. Another surprising and unexpected feature of the invention is that despite the presence of silver, the antimicrobial powders can used for making, for example, substantially white nylon fibers. Without wishing to be bound by any theory or explanation, it is believed that the desired color of the present composition is achieved by using relatively low effective amounts of the coloring components, e.g., silver. Anatase titania is normally preferred over rutile if relatively low levels of abrasity are desired.

The next successive coating upon the antimicrobial component is a protective coating consisting essentially of silicon dioxide. The protective coating functions as a barrier between the antimicrobial component and the matrix into which the antimicrobial powder may be incorporated. For example, when the antimicrobial powder is incorporated within a polymeric matrix, the protective coating minimizes any interaction with the polymer, e.g., in the absence of the protective coating the antimicrobial component could be reduced chemically by the polymeric matrix at the relatively high shaping temperatures. The protective coating also is believed to influence the rate at which the antimicrobial component diffuses from a dispersed coated particle into the surrounding matrix, e.g., a nylon fiber.

The protective coating layer normally corresponds to about 0.2 to at least about 5% by weight based on the core material, and usually about 1% to about 3% by weight of the coated particle composition. It will be appreciated by those skilled in the art that if relatively fine core particles are employed when practicing the invention, then the practitioner should ensure substantially total surface coverage of the first coated core material. While the protective layer of silica can be quite dense, the protective layer should be sufficiently porous to permit diffusion of the antimicrobial component through the coating at an effective rate and function as a barrier that limits, if not eliminates, interaction between the antimicrobial component and a surrounding matrix.

The next successive coating layer is a dispersion enhancing coating such as a hydrous metal oxide, e.g., alumina, hydrous alumina, zirconia, mixtures thereof, among others. This coating corresponds to about 0.1% to at least about 5% by weight and normally about 1 to about 3% by weight based on the core material. When the metal oxide consist essentially of hydrous alumina, the alumina is typically a mixture of boehmite (AlOOH) and amorphous alumina ($Al_2O_3H_2O$). Without wishing to be bound by any theory or explanation, it is believed that the hydrous metal layer functions to control the dispersion and dispersion stability of the antimicrobial powder. It is also believed that the resulting hydrophilic nature of the antimicrobial powder is also beneficial in facilitating the dispersion and/or flocculation of the particulate compositions during manufacture of the antimicrobial powders and enhance the dispersion of the powders into a matrix material.

Finally, a suitable dispersion aid such as a suitable resin (e.g., nylon 66/6-10/6 resin sold under the trademark Elvamide®), trimethylolpropane, dioctyl azelate, among others, is coated onto the antimicrobial powder composition in order to enhance dispersion of the powder in end use applications. The dispersion aid can be a residual micronizing aid from a previous processing step. While any suitable dispersion aid can be employed, effective amounts of dioctyl azelate are normally preferred. The presence of an effective amount of a dispersion aid is useful for improving the antimicrobial powder compounding rate into polymer systems and forming more uniform dispersions. The amount of a dispersion aid that is present in the antimicrobial composition ranges between about 0.1% and at least about 2.0% by weight based upon the antimicrobial powder, with about 0.5% to about 1% by weight normally being effective.

Without wishing to be bound by any particular theory or explanation, it is believed that using an antimicrobial composition consisting essentially of a mixture of inorganic core particles that have different indices of refractions allows one to control the level of antimicrobial activity and obtain the desired level of delustering. Blending at least two core particles with differing indices of refraction allows formulating mixtures to achieve a wide range of fiber characteristics that range from virtually transparent (non-delustered) to delustered while maintaining a high level of antimicrobial activity. It will be appreciated by those skilled in the art that the ratio of the titanium dioxide to zinc oxide to barium sulfate mixture can vary widely and is dependent upon the appropriate level of delustering desired and may be readily selected by the artisan. Antimicrobial compositions, which contain relatively large quantities of barium sulfate, that are incorporated into a polymer matrix, tend to produce an polymeric article that is more transparent than articles that contain relatively large quantities of titania.

The process for preparing the antimicrobial composition of the invention is described in greater detail in U.S. Pat. No. 5,180,585; the disclosure of which was incorporated herein by reference. Generally, the antimicrobial powder composition is prepared by a process comprising the steps of:

(a) forming an aqueous suspension of titanium dioxide, zinc oxide or barium sulfate particles;

(b) precipitating a coating layer of an antimicrobial component on said particles wherein the precipitated antimicrobial coating is silver, in some cases followed by precipitating other antimicrobial components such as copper (II) oxide;

(c) adding an alkali metal silicate and maintaining the pH between about 5 to 9 to deposit a protective coating layer of silica;

(d) adding a precursor to a hydrous metal oxide such as sodium aluminate to the agitated aqueous suspension at a temperature between about 60° C. and 90° C. while controlling the pH within the range of about 6 to 11, usually about 8 to 8.5 to effectuate the next successive coating layer of hydrous metal oxide, e.g., alumina or boehmite AlOOH and amorphous alumina $Al_2O_3$ $H_2O$;

(e) recovering the product and substantially removing soluble salts;

(f) drying the product at a temperature of about 120° C.;

(g) intimately mixing the product with dioctyl azelate in standard equipment such as a "v" or ribbon blender; and (h) passing the product through a commercially available micronizer with superheated steam or air. It would be appreciated by those skilled in the art that a dispersion aid such as dioctyl azelate could also be added simultaneously with the product through a micronizer for enhancing the micronization process.

When barium sulfate and/or titania particles are coated with copper and zinc compounds, such compounds are also precipitated onto these particles either simultaneously or separately. Normally, the copper and zinc compounds are precipitated in an aqueous medium as insoluble species onto the particles by using any suitable method, e.g., acid/base precipitation chemistry.

The titanium dioxide based product is normally recovered as a dry powder. The procedure is repeated as desired by forming an aqueous suspension of barium sulfate or zinc oxide particles. Then an antimicrobial component coating layer, e.g., silver, is precipitated on said barium sulfate or zinc oxide particles. Steps (c)–(h) are repeated as desired. Normally, barium sulfate is coated with silver, followed by zinc and/or copper compounds such as zinc oxide, zinc silicate and copper oxide, then silica, then alumina, and finally with dioctyl azelate. In the case of zinc oxide particles, typically the first coating is silver, then silica, then alumina, and finally dioctyl azelate. The barium sulfate and/or zinc oxide based product is recovered as a dry powder. For example, zinc oxide particles can be coated with successive coatings of silver, silica, alumina and a dispersion aid by using the procedure described above. At least two coated powders can be blended by any suitable method to form the desired antimicrobial composition.

The blended product is easily dispersible within a polymer matrix and can be virtually transparent. The blended product further exhibits a desirable low color, i.e., whiteness, when producing a shaped polymeric article (e.g. a fiber) and maintains a high level of antimicrobial activity as exemplified hereinafter. Low color as determined by Delta E is a desirable characteristic for a fiber additive because the absence of color enhances the ability of a fiber to be dyed. Delta E is the deviation from whiteness and is a function of three coordinates as described hereinafter. The antimicrobial powders of the invention can be incorporated into fibers such as nylon, spandex, polyester among others in order to form an antimicrobial fiber that has a controlled luster, and whiteness.

A further aspect of this invention relates to polymer articles having antibacterial properties by virtue of the particulate antimicrobial composition being incorporated into the polymer matrix.

The organic polymers from which the articles can be fabricated include synthetic, natural and semi-synthetic organic polymers. Examples of polymers that can be used to practice this invention are aliphatic and aromatic polyamides including nylon 6, segmented polyurethane elastomers, spandex or elastane elastomers, mixtures thereof, among others. "Spandex" is defined herein to refer to a fiber or filament made from a long chain synthetic polymer that comprises at least 85% by weight of a segmented polyurethane. (Spandex fibers are sold by the DuPont Company under the Lycra® Trademark).

A polymer article of the invention having antimicrobial properties can be comprised of the aforementioned particulate antimicrobial composition and at least one organic polymer. The antimicrobial composition accounts for about 0.05% to about 40% by weight, normally 0.1% to 5% by weight of the polymer article and usually about 0.1% to about 1%.

If the antimicrobial composition is incorporated in an amount less than about 0.05% by weight, then the polymer article has a tendency to have an insufficient antimicrobial activity for any useful applications. However, it will be appreciated by those skilled in the art that if extremely fine particles are incorporated into the polymer matrix, then less than about 0.05% may be acceptable. Above about 40% by weight, e.g., above about 60% by weight, there is no significant increase in the antimicrobial activity of the polymer article and the physical properties of the polymer article can exhibit some deterioration. This also limits the usefulness of the article. Furthermore, the incorporation of high levels of the antimicrobial composition can be undesirable from an economic standpoint and because of undesirable effects on the properties of the resultant article. A typical upper level for the antimicrobial component is about 5% weight below which level there is usually an optimum combination of antimicrobial activity, polymer article properties and cost-efficiency.

The polymer articles according to the present invention may contain other additives as well as the antimicrobial composition. They may contain, for example, polymerization catalysts, stabilizers, delustering agents, optical whitening agents, organic or inorganic pigments, inorganic fillers, plasticisers, among other additives. In some cases, the antimicrobial particles themselves can fulfill a dual role and provide the benefits of some of the aforementioned additives.

Polymeric articles can be prepared by adding the antimicrobial powder of the invention to a monomer and/or to an intermediate product normally prior to polymerization. For best results, the antimicrobial powders are mixed or compounded with a so-called master batch prior to shaping the compounded master batch into a useful article. While any suitable master batch can be employed, the antimicrobial powders of the invention can be dispersed into a conventionally used master batch, e.g., about 25% by weight of the powders is admixed with the polymeric phase prior to fabricating of the desired polymeric article. An antimicrobial composition that has been tailored to impart the desired characteristics to the surround polymeric matrix, can be compounded into the master batch and, thereafter used for making useful antimicrobial polymeric articles. The compounded master batch can be used for fabricating polymeric articles using any conventional procedure.

In one aspect of the invention, an antimicrobial composition consisting essentially of barium sulfate core particles that are coated successively with about 0.2% by weight silver, about 0.4% zinc silicate, about 2.0% silica, about 2.2% alumina, and about 0.5% dioctyl azelate, can be employed for making spandex fibers. In some cases, antimicrobial powders containing zinc compounds such as zinc oxide and/or zinc silicate also functions to impart chlorine resistance to the spandex fiber. The antimicrobial composition can be introduced into the Spandex manufacturing process by using the method disclosed in U.S. Pat. No. 5,028,642; the disclosure of which is hereby incorporated by reference. This method can be used for making an antimicrobial fiber that has a Delta E which is typically less than about 15; usually about 5.

In another aspect of the invention, an antimicrobial powder composition consisting essentially of titania core particles that are successively coated with about 0.95% by weight silver, about 0.8 copper oxide, about 0.8 zinc silicate, about 2.0% silica, about 2.2% alumina, and about 0.5% dioctyl azelate, can be employed for making nylon staple and tow. An antimicrobial composition consisting essentially of barium sulfate particles, having the successive coatings identified previously in this paragraph, is particularly useful for use in making nylon 6,6 fibers and nylon 6,12 fibers or bristles. A suitable master batch consist essentially of less than 40%, normally less than 15% by weight of the previously identified antimicrobial compositions, about 10 to about 20% by wt. Elvamide® 6, and about 50 to about 60% nylon 6. The compounded master batch can be used for making antimicrobial nylon fibers that have a Delta E which ranges from about 5 to about 15.

In yet another aspect of the invention, an antimicrobial powder composition consisting essentially of zinc oxide core particles that have been coated successively with about 0.2% by weight silver, about 2.0% silica, about 2.2% alumina and about 0.5% dioctly azelate, can be employed for making nylon fibers, e.g., nylon 6,6 or 6, that are used for making flooring systems, e.g., carpeting. When a solution dyed carpeting system is desired, an antimicrobial powder consisting essentially of barium sulfate particles that are successively coated with about 0.95% silver, about 0.8% copper oxide, about 2.0% silica, about 2.2% alumina, and about 0.5% dioctyl azelate, is particularly useful. Further, the antimicrobial powders can be introduced into carpet yarn, backing such as foams, latex, pad, adhesives, among other carpet components, in order to obtain an antimicrobial carpet system.

In addition to making shaped polymeric articles, the antimicrobial powders of the invention can be used to provide antimicrobial properties to virtually unlimited array of articles such as personal care products such as cosmetics, polymeric systems including films for use in packaging materials, appliances, water supply systems, air conditioning filtration systems, pond and pool liners, building materials such as adhesives, sealants, grout, caulking, roofing materials, siding, ceiling tiles, medical devices, among other articles wherein the presence of microorganisms is undesirable. For example, the antimicrobial powders of the invention can be added onto or into nylon particles that are used for making cosmetic products. Further, the antimicrobial powders of the invention can be incorporated within fibers that are employed to make shoe interlinings, swim wear, military uniforms, socks, bedding materials such as mattress covers, sheets, and blankets, clothing interliners, towels, umbrellas, wipes, marine fabrics, tents, awnings, upholstery, outdoor furniture coverings, filters, hospital fabrics such as gowns, caps, coverings, and drapes, bandages, medical packaging fabrics, diapers, sanitary products such as napkins, among others. The antimicrobial powders can also be incorporated with polymeric systems for making plastic films, containers and bottles for use in food, medical and pharmaceutical packaging, filaments used for making tooth, cosmetic, and paint brushes, plastic bag such as for contaminated waste products, garbage bags and containers, and shower curtains, among others. Antimicrobial powders can be used to make coatings that are used in marine paint, architectural coatings, industrial coatings, powder coatings, exterior house paints, paints for use in hospital and health care facilities, among others. By selecting an appropriate mixture of antimicrobial powders, a virtually unlimited array of products can be obtained that possess tailored color, luster and antimicrobial characteristics.

Preparing Polymer Samples for Testing

For polymeric materials that are stable in a melt and whose melt viscosity is relatively low (e.g., nylon 6,6), melt spinning is the preferred method for making fibers. Using a conventional single position, continuous (extrude, draw, bulk and windup) unit, a 25% concentrate of Elvamide®/nylon 6, and an antimicrobial powder (e.g., a 40% $TiO_2$/60% $BaSO_4$ blend that was about 25% by weight of the concentrate) were injected into nylon 6,6 at the screw melter and spun into carpet yarns. The nylon 6,6 pellets were fed by gravity from a hopper above the screw melter. The desired level of antimicrobial concentrate in yarn was obtained by adjusting the concentrate feedrate with respect to concentrate level and thruput of the nylon 6,6 matrix polymer. For example, to obtain about 0.1 wt. % antimicrobial powder in the yarn, feedrate was set at about 0.34 pounds per hour (PPH) for a polymer thruput of about 84 PPH and a 25% concentrate. Processing parameters were similar to those typically used for nylon 6,6. The yarn containing the additive was extruded through a spinneret into filaments which were then drawn, bulked and wound by using conventional techniques. The wound fibers were then collected for antimicrobial testing.

Shake Flask Test for Antimicrobial Activity

Antimicrobial activity of the fibers described above was measured using the Shake Flask Test described generally in U.S. Pat. No. 4,708,870 and outlined in Malek and Speier, The Journal of Coated Fabrics, Vol. 12, July 1982, pp. 38–45; the disclosure of both of these references is hereby incorporated by reference.

The Shake Flask Test normally requires the test material to be in a form having a high surface area to weight ratio. Articles having the form of powders, fibers, and thin films have also proven to be acceptable.

The bacterial inoculum for the Shake Flask Test was prepared by transferring about 2.0 ml of an overnight broth culture into a 300 ml nephyloculture flask (supplied by Bellco Glass Inc., Vineland, N.J.) containing about 100 ml of Tryptic Soy Broth (TSB) (supplied by Remel, Lexena, Kans.). The flask was incubated at a temperature of about 37° C. while being shaken (at about ca. 200 rpm). Growth of the culture was determined during incubation by using a Klett-Summerson photoelectric colorimeter (supplied by Klett Mfg. Co., NY, N.Y.). When the culture reached late-log phase (about 185–200 Klett units for *Klebsiella pneumoniae* ATCC Registration No. 4352), dilutions were prepared with a sterile 0.2 mM phosphate buffer (pH about 7) to obtain an inoculum.

The inoculum was placed into a sterile, disposable 250 ml Erlenmeyer flasks (supplied by Corning Glass Co., Corning, N.Y.) that contained about 0.75 g of the antimicrobial composition of the invention or a suitable control material as indicated below. Each flask contained a known concentration of bacteria in a final volume of about 75 ml phosphate buffer.

The initial concentration of bacteria used in the various examples was determined by serial dilution of the inoculum (about 0.2 mM Phosphate buffer, pH 7) and plating in triplicate on Trypticase Soy Agar (TSA) plates (supplied by BBL, Cockeysville, Md.). The flasks were shaken on a Burrell wrist action shaker (supplied by Burrell Corp., Pittsburgh, Pa.). An approximately 1.2 ml aliquot was removed from each flask after shaking for about 1 hour (or other appropriate time interval as indicated). Duplicate petri plates containing the TSA plates were inoculated via spread plating with about 0.1 ml each of the 1.2 ml aliquot sample. The remaining 1.0 ml was serial diluted and plated in duplicate. The TSA plates were incubated at a temperature of about 37° C. for about 18 to 24 hours. Plates having between about 30 and 300 colonies were counted and the bacterial concentration determined from the mathematical mean of the plate counts. If none of the plates contained at least 30 colonies, then all colonies were counted and the bacterial concentration determined from the mathematical mean of the plate counts. Should the plate count be below the limit of detection of the procedure described herein, the colony count was said to be zero.

Antimicrobial activity was determined by the formulas:

$kt = \log 10(Co) - \log 10(Ct+1)$ $Dt = \log 10(CFt) - \log 10(Ct+1)$ where:

Co=initial concentration of bacteria (cfu/ml) in test flask at time zero

Ct=concentration of bacteria (cfu/ml) in test flask at time t (one is added to the number to avoid calculating the log of zero), CFt=concentration of bacteria (cfu/ml) in control flask at time t, and cfu/ml=colony forming units per milliliter.

The relationship between percent reduction and log reduction is conveniently seen by reference to the following:

| % Reduction | Kt | Log Reduction |
| --- | --- | --- |
| 90 | 1 | 1 |
| 99 | 2 | 2 |
| 99.9 | 3 | 3 |
| 99.99 | 4 | 4 |
| 99.999 | 5 | 5 |

In all the Examples, the polymeric material was tested substantially free of fiber finish.

The present invention is further described in the following examples and comparative showings which illustrate the advantages of the invention. These examples are provided only to illustrate the invention and are not to be construed as limiting in any way the scope of the invention.

EXAMPLES 1–5

Examples 1–5 describe preparing $TiO_2$ (A)/$BaSO_4$ (40/60 blend) core particles wherein the $TiO_2$(A) and $BaSO_4$ particles are both coated successively with either approximately 0.2% by weight Ag or 1% of Ag, 0.4% CuO, 2% $SiO_2$, 2.2% $Al_2O_3$ and 1% dioctyl azelate.

About 12 liters of distilled water were placed into a 17 liter glass vessel that was equipped with a stirring paddle and mounted on a heating plate. The water was heated to a temperature of about 75° C. Approximately 3000 grams of $BaSO_4$ powder (supplied by Sachtlen), was added to the glass vessel and stirring established to form a relatively smooth slurry of the $BaSO_4$ powder. The $BaSO_4$ index of refraction was 1.64. Approximately 56.25 grams of $AgNO_3$ dissolved into about 50 ml distilled water was added slowly to the slurry over a 15 minute period. During this addition an approximately 20% NaOH solution was added drop-wise to control the pH between about 8.5 and 9.0.

About 37.5 grams of $NaNO_2$ that was dissolved into about 100 ml water was added to the stirred slurry over a 30 minute period to cause the reduction of Ag+to Ag. The slurry system was then held at a pH of about 9 for about 15 minutes in order to establish equilibrium. Approximately 22.5 grams of $Cu(NO_3)$ $3H_2O$ in 200 ml distilled water was added to the stirred slurry system over a period of about 1 hour and the pH was controlled at about 8.2 with 20% NaOH solution.

Approximately 276 grams of $K_2SiO_3$ solution was diluted to about 500 ml with distilled water and added to the stirred slurry system over an about 1 hour period controlling the pH at 9.5 with 20% HCl solution. After the addition, the slurry was stirred for about 15 minutes while maintaining the temperature of the slurry at about 75° C. and a pH of about 9.5 in order to establish equilibrium. After establishing equilibrium, approximately 180 ml of $Na(OH)_4$ solution (0.365 gr. $Al_2O_3$/ml.) was added to the stirred slurry over a 1 hour period while maintaining the pH at about 8.2 by adding 20% HCl. The slurry was then stirred at a pH of about 8.2 for approximately 30 minutes in order to establish equilibrium and form a slurry of coated particles.

The coated particles were filtered on a Buchner filter, washed substantially free of soluble salts and ions and then dried at a temperature of about 120° C. for a period of about 16 hours. The dried coated $BaSO_4$ was mixed with about 1% by weight dioctyl azelate in a V-Blender. Prior to mixing the dioctyl azelate, the dioctyl azelate was dissolved into about 100 ml of methanol to assure good distribution. If desired, other alcohols could be used instead of methanol. The mixed product was dried at a temperature of about 120° C., sieved through a 20 mesh screen and steam micronized in a commercially available 8 inch micronizer using about 3 pounds of steam per pound of coated $BaSO_4$.

The above procedure was repeated for coating the $TiO_2$ particles (supplied by Sachtleben as Anatase $TiO_2$ Grade LW-SU). The $TiO_2(A)$ index of refraction was about 2.52. For $TiO_2$ having a coating containing about 0.2% by weight Ag that was obtaining by using substantially the same procedure and approximately 11.25 grams $AgNO_3$ and 7.5 grams $NaNO_2$.

The powders produced by Examples 1–5 were examined for chemical analyses; the results are shown below in Table 1.

TABLE 1

| Example | 1 | 2 | 3 | 4 | 5 |
|---|---|---|---|---|---|
| Ag on $TiO_2$ (A) | 0.2 wt % | 0.2 | 0.2 | 1 | 1 |
| Ag on $BaSO_4$ | not added | not added | not added | 1 | 1 |
| CuO | 0.4 wt % | 0.4 | 0.4 | 0.4 | 0.4 |
| $SiO_2$ | 2 wt % | 2 | 2 | 2 | 2 |
| $Al_2O_3$ | 2.2 wt % | 2.2 | 2.2 | 2.2 | 2.2 |
| dioctyl azelate | 1 wt % | 1 | 1 | 1 | 1 |

Preparation of $TiO_2/BaSO_4$ Blends-Making Nylon Fibers

A. The coated particles formed substantially in accordance Examples 1–3 were used for preparing a concentrate according to the following procedure:

A concentrate containing a desired level of coated particle was prepared by mixing the appropriate weight of coated $TiO_2$ particles, with nylon 66/6-10/6 resin (sold by the DuPont Company under the trademark Elvamide®). The Elvamide® particle mixture was then introduced into a nylon 6 master batch. The nylon 6 mixture was then extruded through a commercially available twin-screw extruder to yield pellets about ¼ inch in length. For example, to make a 25% concentrate, coated $TiO_2$ powder was dispersed into Elvamide® that produced a 30/70 powder/Elvamide® mixture. This mixture was then introduced into the nylon 6,6 to give a 25% concentrate or master batch, i.e. the $TiO_2$ was 25% by weight of the nylon 6,6.

B. The coated particles formed substantially in accordance with Examples 4–5 were used for preparing a blend according to the following procedure:

Each of the powders was compounded separated to 25% concentrates using Elvamide® as the dispersing aid and nylon 6 as matrix for the concentrate. The individual concentrates were then physically mixed together to give the desired blend level. For example, to obtain the 40/60 concentrate blend, 40% by weight of the $TiO_2$ concentrate was mixed with 60% by weight of coated $BaSO_4$ concentrate by shaking these particles together in a plastic bag. No further mixing was undertaken prior to spinning of these mixed pellets into nylon 6,6.

Antimicrobial Activity of Antimicrobial Compositions in the Shake Flask Test

Using the previously procedure for performing the shake flask test, the antimicrobial compositions were incorporated into a Nylon 66 carpet yarn that was evaluated for microbe activity. The activity against *Klebsiella pneumoniae* is shown in Table 2.

Color Analyses and Luster Ratings

The universe of color is a combination of three elements, value ("lightness", ranging from dark to light), hue ("color", red, yellow, green, etc.), and chroma ("saturation", varying from dull to vivid). In three dimensional space, these color coordinates can be expressed as L* (black to white), a* (green to red), and b* (blue to yellow). It is important to note that the combination of coordinates a* and b* determine hue and chroma [$C^*=sqrt(a^{*2}+b^{*2})$] while L* is a measure of value. L* values refer to the lightness or darkness of the sample, with 100 being very light and zero being very dark. A positive value for a * means red, while a negative value means green. A positive value for b* means yellow, while a negative value means blue.

Delta E is the deviation from whiteness and is determined by the L*, a* and b* coordinates. Delta E under Cool White Fluorescence (CWF) was calculated to show the antimicrobial powder does not adversely affect yarn color and is shown in Table 2.

In order to report the color of the Nylon fiber as distance from whiteness, the L*, a* and b* values are used to calculate a vector sum. The vector sum is obtained by subtracting the L* value from 100, taking the square of this difference, adding this to the squares of the a* and b* values. The square root of this sum is then taken, and then this value is subtracted from 100. The final number is the distance from whiteness.

Color values of the Nylon fibers were measured in a conventional manner by using an ACS Spectrophotometer (available from Applied Color systems, Inc., Princeton, N.J.). The fibers or yarns to be tested are wound onto a 3in X 3in gray card, a sufficient number of times to generate a thickness such that the card was not visible behind the fiber when exposed to the light source of the spectrophotometer. The cards are then placed into the Spectrophotometer of the instrument for reading the color values. For color matching, color values are read against a standard, i.e., yarn containing no additive. Readings are made using CWF (cool white fluorescent) as a standard for the light that was used for illuminating the yarn. Each reading yields five color coordinate values, i.e., L* (light/darkness scale), a* (red/green scale), b* (yellow/blue scale), C* (brightness), and h (hue or color). The first three L*, a*, and b*, make up the CIELAB coordinate system and the last two C* and h, make up the color measurement committee of the Society of Dyers and Colorists (CMC) coordinate system. When using the CIELAB, (standardized by C. I.E., the Commesseon International de L'Eclairage) the Delta E, i.e., total color difference between two samples, was obtained by taking the difference between the L*, a*, and b* coordinates.

The Luster Rating of the Nylon fiber is also shown in Table 2. The Luster Rating was made by a visual determination that was performed by comparing experimental fibers to another fiber having a standardized luster rating.

TABLE 2

| Example | TiO$_2$/BaSO$_4$ % in Yarn* | 1 Hour Kt | 24 Hour Kt | Delta E (CWF) | Luster** Rating |
|---|---|---|---|---|---|
| 1 | .04/0.0 | −0.02 | −0.43 | 0.95 | 1 |
| 2 | .08/0.0 | −0.01 | −0.48 | 0.19 | 1 |
| 3 | 0.2/0.0 | −0.07 | −0.24 | 3.65 | 4 |
| 4 | .04/.06 | −0.06 | 4.89 | 6.45 | 1 |
| 5 | .08/.12 | 0.08 | 4.89 | 14.55 | 2 |

*Percentage of antimicrobial blended powder in the yarn
**Scale: Bright = 1, Mid-Dull = 3, and Semidull = 5

These data demonstrate the combination of high antimicrobial activity against *K. pneumoniae*, acceptable color and luster control afforded by the composition of this invention. An effective 24 hour Kt is normally at least about 1.0 and normally approaching 5.0. The negative 24 hour Kt for Examples 1–3, indicates microbial growth, is expected based on the relatively low concentration of coated TiO$_2$ particles in the yarn and low loading of silver on the particles. However, note that by blending particles with a higher loading of silver on the blended particles, high antimicrobial activity can be obtained at a low concentration of particles in yarn without sacrificing color or luster, e.g., by blending coated titania and barium sulfate particles. Luster can further be controlled by varying the blend level. These data further show that the low delustering of Example 4 due to the relatively low refreactive index of barium sulfate.

COMPARATIVE EXAMPLES A and D

The shake flask, color data and level of deluster for commercially available Bactekiller AC® (supplied by Kanebo Zeolite U.S.A., Inc.), a zeolite having 3.1% Ag and 5.5% Cu is shown in Table 3. The Bactekiller AC® was incorporated into the nylon fiber substantially in accordance with the method described above.

COMPARATIVE EXAMPLES B AND E

This example describes the preparation TiO$_2$(A) having successive coatings of 1% Ag, 0.4 wt % CuO, 2% SiO$_2$, 2.2% Al$_2$O$_3$ and 1 wt % dioctyl azelate. Substantially the same procedure described above for preparing Examples 1–3 was used to make the coated particle used in this Comparative Example. The data are shown in Tables 3 and 4.

COMPARATIVE EXAMPLES C AND F

This example describes the preparation of BaSO$_4$ having successive coatings of 1% Ag, 0.4 wt % CuO, 2% SiO$_2$, 2.2% Al$_2$O$_3$ and 1 wt % dioctyl azelate. Substantially the same procedure described for Examples 1–3 was used. The Delta E was obtained by using the CIELAB Scale. The data are shown in Tables 3 and 4.

TABLE 3

| Example | % in Yarn | 1 Hour Kt | 24 Hour Kt | Delta E (CWF) | Luster Rating |
|---|---|---|---|---|---|
| A | 0.3 | 1.09 | 5.02 | 32.52 | 1 |
| B | 0.3* | 0.36 | 4.98 | 13.56 | 3 |
| C | 0.3 | 0.34 | 4.98 | 12.94 | 2 |

These data demonstrate that commercially available Bactekiller AC® and single core particles do not obtain the combination of properties, e.g., high antimicrobial activity, small deviation from whiteness and the desired level of delustering. In particular, Example A of Table 3 demonstrate that commercially available materials fail to achieve a desirable whiteness, e.g., compare the Delta E or distance from whiteness values of Table 2 to Table 3. While Examples B and C achieved an acceptable Delta E and 24 Hour Kt, such was obtained by using relatively large quantities of antimicrobial powder in the yarn. In comparison, smaller quantities of antimicrobial powders can be used in the blend to give equivalent antimicrobial activity with improved color and luster (Example 4 of Table 2) or with no sacrifice of luster or color (Example 5 of Table 2).

TABLE 4

| Example | % in Yarn* | 1 Hour Kt | 24 Hour Kt | Delta E | Luster Rate** |
|---|---|---|---|---|---|
| D | 0.1 | 0.50 | 5.19 | 10.29 | 1 |
| E | 0.1 | 0.16 | 2.82 | 9.72 | 2 |
| F | 0.1 | 0.16 | 4.98 | 8.48 | 0 |

*percentage of the BaSO$_4$ particles in the Yarn
**Visually Determined Luster Rating The above data demonstrate further that even at relatively low concentrations of additive in the yarn Bactekiller AC® and single core particles do not obtain the desirable combination of properties, e.g., high antimicrobial activity, small deviation from whiteness and luster rating, that can be achieved by employing the inventive blend of powders. When compared to Example 4 of Table 2, both Bactekiller AC® and single core particles have poorer color versus the blend. As shown by Example F, coated barium sulfate is a non-delustering particle because the refractive index of barium sulfate is substantially equivalent to that of the polymer.

What is claimed is:

1. An antimicrobial composition consisting essentially of coated core particles wherein the core particles consist essentially of a mixture of at least two members selected from the group consisting of titania, barium sulfate and zinc oxide that have an average diameter between about 0.005 to about 3.0 microns, wherein said core particles are coated successively based upon said particles, with (a) about 0.2 to at least about 1 weight % silver, (b) about 0.2 to at least about 0.8 weight % of at least one member from the group of zinc, zinc oxide, zinc silicate, copper, and copper (II) oxide, (c) about 0.2 to 5 weight % of a protective coating; (d) about 1 to at least about 3 weight % of a dispersion coating; and Led about 0.2 to 3 weight % of a dispersion aid.

2. An antimicrobial composition consisting essentially of about 40 to 60% titania particles and about 40 to 60% barium sulphate particles wherein both of said particles are successively coated based upon said particles, with about 0.2 to 1% wt. Ag, about 0.2 to about 0.8% CuO, about 0.2 to about 5% SiO$_2$, about 1 to about 3% Al$_2$O$_3$; and about 0.2 to 3% dioctyl azelate.

3. The composition of claim 1 wherein the protective coating is silica.

4. The composition of claim 1 wherein the dispersion coating is alumina.

5. The composition of claim 1 wherein the dispersion aid is at least one member from the group of dioctyl azelate and trimethylolpropane.

6. The composition of claim 1 wherein one of the core particles is zinc oxide that is coated successively with silver, silica, alumina and dioctyl azelate.

7. The composition of claim 1 wherein the mixture of inorganic particles is titania and barium sulfate that are coated successively with silver; at least one member selected from the group consisting of copper oxide, zinc silicate and zinc oxide; silica; alumina; and dioctyl azelate.

8. In an antimicrobial, shaped polymer article, a polymeric carrier matrix comprising at least one polymer and about 0.1% to at least about 5% by weight, based on the total weight of the shaped polymer article, of the antimicrobial composition of claims 1, 6, 7 or 2.

9. The antimicrobial, shaped polymer article of claim 8 wherein the polymeric carrier matrix is a fiber.

10. The antimicrobial, shaped polymer article of claim 8 wherein the polymer is at least one polymer selected from the group consisting of nylon 6,6, nylon 6,12 and spandex.

11. The antimicrobial, shaped polymer article of claim 8 wherein the whiteness of the article is defined as having a Delta E of less than about 15.

12. A compounded master batch for use in making a fiber comprising (a) nylon 66/6-10/6 resin, (b) nylon 6,6, and (c) an effective amount of the antimicrobial powder of claims 1, 6, 7 or 2.

13. The antimicrobial, shaped polymer article of claim 8 or 11 wherein the antimicrobial activity of the article is defined by a 24 Hour Kt of at least about 1.0.

* * * * *